(12) United States Patent
Ginsberg et al.

(10) Patent No.: US 8,580,494 B2
(45) Date of Patent: Nov. 12, 2013

(54) METHODS AND COMPOSITIONS FOR AMPLIFICATION AND DETECTION OF MICRORNAS

(75) Inventors: Stephen D. Ginsberg, Wynnewood, PA (US); Shaoli Che, Stony Point, NY (US)

(73) Assignee: Research Foundation For Mental Hygiene, Inc., Menands, NY (US)

( * ) Notice: Subject to any disclaimer, the term of this patent is extended or adjusted under 35 U.S.C. 154(b) by 109 days.

(21) Appl. No.: 11/844,695

(22) Filed: Aug. 24, 2007

(65) Prior Publication Data

US 2008/0051296 A1 Feb. 28, 2008

Related U.S. Application Data

(60) Provisional application No. 60/823,624, filed on Aug. 25, 2006.

(51) Int. Cl.
*C12Q 1/68* (2006.01)

(52) U.S. Cl.
USPC .................................. 435/6.1; 506/7

(58) Field of Classification Search
None
See application file for complete search history.

(56) References Cited

U.S. PATENT DOCUMENTS

| | | | | |
|---|---|---|---|---|
| 5,162,209 A | * | 11/1992 | Scheele | 435/91.41 |
| 5,580,730 A | * | 12/1996 | Okamoto | 435/6 |
| 5,795,714 A | * | 8/1998 | Cantor et al. | 435/6 |
| 6,593,120 B1 | * | 7/2003 | Riggs et al. | 435/194 |
| 2006/0099619 A1 | * | 5/2006 | Remacle et al. | 435/6 |

FOREIGN PATENT DOCUMENTS

| WO | WO 2005003318 | * | 1/2005 |
|---|---|---|---|
| WO | WO 2005/098029 | * | 10/2005 |

OTHER PUBLICATIONS

Nichols et al. Current Protocols in Molecular Biology. Supplement 84: pp. 3.13.1-3.13.8; 2008.*
Elbashir et al (2001 Genes & Development 15:188-200).*

* cited by examiner

*Primary Examiner* — Christopher M Babic
*Assistant Examiner* — Karen S Weiler
(74) *Attorney, Agent, or Firm* — David L. Nocilly; Bond Schoeneck & King PLLC

(57) ABSTRACT

A method and system for amplifying non-coding RNA, microRNA, and small polynucleotide sequences through the generation of a pool of signature sequences to the target sequences. The target sequences can be amplified through DNA synthesis, RNA synthesis, or the combination of DNA and RNA synthesis. The amplification of signature sequences provides an efficient and reproducible mechanism to determine the presence or absence of the miRNAs, to analyze the quantities of the target miRNAs, and for miRNA profiling. The method may also be used for screening for unknown non-coding RNAs, including novel miRNAs.

19 Claims, 9 Drawing Sheets

SEQUENCE LISTING

<160> NUMBER OF SEQ ID NOS: 6

<210> SEQ ID NO 1
<211> LENGTH: 61
<212> TYPE: DNA
<213> ORGANISM: Mus musculus

<400> SEQUENCE: 1
aacgaggaat gcggccagtg aattgtaata cgactcacta taggatcata cagctagata    60
a                                                                   61

<210> SEQ ID NO 2
<211> LENGTH: 72
<212> TYPE: DNA
<213> ORGANISM: Mus musculus

<400> SEQUENCE: 2
ggcgcgccga attcttcata ctcatacgtt atctagcttc tttggttatc tagcttcttt    60
ggttatctag ct                                                       72

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
agctagataa ccaaagaa                                                 18

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ggccagtgaa ttgtaatacg a                                             21

<210> SEQ ID NO 5
<211> LENGTH: 56
<212> TYPE: DNA
<213> ORGANISM: Mus musculus
<220> FEATURE:
<221> NAME/KEY: misc_feature
<222> LOCATION: (46)..(56)
<223> OTHER INFORMATION: n is a, c, g, or t

<400> SEQUENCE: 5
aacgaggaat gcggccagtg aattgtaata cgactcacta taggannnnn nnnnnn       56

<210> SEQ ID NO 6
<211> LENGTH: 26
<212> TYPE: DNA
<213> ORGANISM: Mus musculus
<220> FEATURE:
<221> NAME/KEY: misc_feature
<222> LOCATION: (15)..(26)
<223> OTHER INFORMATION: n is a, c, g, or t

<400> SEQUENCE: 6
ggcgcgccga attcnnnnnn nnnnnn                                        26

METHODS AND COMPOSITIONS FOR AMPLIFICATION AND DETECTION OF MICRORNAS

CROSS-REFERENCE TO RELATED APPLICATIONS

The present application claims priority to U.S. Provisional Application No. 60/823,624, filed on Aug. 25, 2006.

STATEMENT REGARDING FEDERALLY SPONSORED RESEARCH OR DEVELOPMENT

This invention was made with government support under grant number NS043939 awarded by the National Institutes of Health (NIH). The government has certain rights in the invention.

BACKGROUND OF THE INVENTION

1. Field of the Invention

The present invention relates to gene amplification and, more specifically, to a method for the linear amplification of small polynucleotides, such as microRNAs.

2. Description of the Related Art

The central dogma of molecular biology and genetics is that within a cell DNA is transcribed into messenger RNA (mRNA) and mRNA is subsequently translated into a corresponding protein. As with many general biological principles, this view appears to be generally valid. Recent evidence, however, including sequencing of the human genome and the continued sequencing of relevant animal models has demonstrated that there appears to be more information in the genome in terms of protein synthesis control than previously realized. Multiple lines of research are beginning to demonstrate that non-protein coding RNAs (ncRNAs) may play a central role in translational regulation. For example, <3% of mRNAs are translated into proteins. Importantly, microRNAs (miRNAs) are a short 17-25-nucleotide (nt) class of RNA molecules that have been shown to have critical functions in a wide variety of biological processes. miRNAs are synthesized from larger miRNA transcripts that fold to produce hairpin structures and serve as substrates for an enzyme of the RNase III family termed cytoplasmic Dicer. They are endogenous noncoding RNAs, which can regulate gene expression of multiple mRNAs. Since the identification of miRNAs in 1993, a growing list of additional miRNAs has been expanding steadily. Approximately 300-400 miRNAs have been identified in human, and each of these miRNAs has been estimated to interact with 5-10 mRNAs. It is estimated that approximately 30% of all expressed genes are regulated by miRNAs. With the exception of certain viruses, most miRNAs reduce gene expression through reduction of the abundance and/or the translational efficiency of target mRNAs.

Studies have shown that miRNAs can be expressed in a tissue-specific or cell-specific manner. Essentially, a mosaic of miRNA expression levels regulates cell growth, differentiation, and other critical parameters throughout various cell types and tissues. miRNA expression levels are controlled tightly during development and are critical for generalized homeostasis. Furthermore, many pathological conditions appear to be related to dysfunction of miRNA expression, including several types of cancer, although this work is in its infancy. miRNA investigation is also being initiated within neurons and dendrites, and it is postulated that miRNA dysfunction has a profound impact on the pathophysiology of neurodegenerative disorders, including Fragile X syndrome, Tourete's symdrome, polyglutamine repeat disorders, as well as Alzheimer's disease (AD) and related dementing illness.

miRNA expression profiling is an ideal method to study expression levels and regulation of individual miRNAs, similar to current paradigms examining mRNA expression levels at the global, regional, and cellular level. However, miRNA profiling poses more challenges than mRNA profiling. One major obstacle when profiling miRNAs is the low expression level. miRNAs are estimated to constitute only 0.001% of total RNA. As a result, large quantities of input RNA are required for miRNA profiling. This requirement makes it difficult to study tissue-specific and cell-type specific expression of miRNAs. Another difficulty of profiling miRNAs is their small size, as they are predominantly 22-25 nt. The small size of miRNAs makes direct amplification difficult with conventional RNA amplification and/or qPCR-based strategies, although several groups have performed modification procedures of RNA amplification methods to identify individual miRNAs in brain. Unlike mRNAs, miRNAs lack an appropriate sequence to anchor a primer for the first strand DNA synthesis, which is typically the first step of the majority of RNA amplification procedures. Moreover, the small size of miRNAs makes them difficult to hybridize to array platforms, because of the unstable hybridization of short oligonucleotides to the complementary sequences. Unfortunately, positive signals generated by short oligonucleotides are generally weak, which reduces the overall detection sensitivity of the assay, and high background is typically a problem due to high concentrations of probe and longer exposure times required for signal detection.

Several methods are currently attempted to amplify miRNAs. In general, these methods attempt to attach a known sequence to target miRNAs through ligation or terminal transferase, which is followed by amplification step through either DNA or RNA synthesis. However, these methods may increase the signal strength but do not substantially increase the sensitivity of the method, because they invariably increase the background nonspecific hybridization. Several methods employ direct labeling of total RNA (presumably including miRNAs) followed by hybridization to immobilized probes. Direct labeling methods suffer from low sensitivity and specificity, and typically require starting material >10-20 ug. To increase the sensitivity and specificity, small RNAs can be enriched via acrylamide gel electrophoresis. The enrichment of small RNAs increases the specificity, but not the sensitivity of miRNA profiling due to the low yield of miRNAs. This method is suitable for Northern blot analysis of individual miRNAs, but may not be sensitive enough for profiling of multiple miRNAs from a small input source. Alternative methods have been employed to increase the signal strength of miRNA species for greater detection capabilities. These approaches include the use of modified nucleic acids, such as locked nucleic acids, to increase the affinity and stability of hybridization to specific probes or using tail labeling methods to increase the number of labeled nucleic acids within miRNA species. Such methods are viable for large quantities of input RNA, but have somewhat limited benefits with small samples due to the relatively nonspecific nature of locked nucleic acid and tail end labeling. Another method to amplify miRNA employs real-time quantitative PCR (qPCR). This method has been demonstrated to be successful for individual miRNAs when sample RNA is abundant. However, qPCR miRNA profiling is difficult to 'scale up for minute quantities of input RNA species, since each miRNA has to be amplified and detected separately. Moreover, the method is difficult to perform with multiple samples and therefore suffers low throughput as compared to medium- and high-throughput array methods. Thus, there is a need for improved miRNA amplification methods that overcome drawbacks in existing methods.

BRIEF SUMMARY OF THE INVENTION

It is therefore a principal object and advantage of the present invention to provide a reliable and reproducible miRNA amplification method for miRNA investigations using small input samples in many diverse disciplines.

It is also a method for the amplification of small polynucleotides encompassing any and all ncRNAs.

It is an additional object and advantage of the present invention to provide a method for the amplification of RNA that may be used to amplify miRNAs.

It is a further object and advantage of the present invention to provide a method for the amplification of miRNA that does not skew the original quantitative relationships.

It is another object and advantage of the present invention to provide a method for the amplification of ncRNAs including microRNAs that has high throughput.

In accordance with the foregoing objects and advantages, the invention provides methods, compositions and kits for amplifying ribo and deoxyribo small polynucleotides, especially, ncRNAs/miRNAs/small polynucleotide sequences through the generation of a pool of signature sequences to the target miRNAs. Through the generation of signature sequences, the target miRNA species can be amplified through DNA synthesis, RNA synthesis, or the combination of DNA and RNA synthesis. The amplification of signature sequences provides an efficient and reproducible means to determine the presence or absence of the target miRNAs, analyze the quantities of the said target miRNAs, and miRNA profiling. With a slight modification of the first oligonucleotides (FON)s and second oligonucleotides (SON)s according to the present invention, the present invention can also be used to screen for unknown ncRNAs including novel miRNAs.

The present invention provides variety of means to amplify target miRNAs, such as DNA synthesis, RNA synthesis, and/or the combination of the said DNA and RNA synthesis. The magnitude of miRNA amplification through the generation of said signature sequences can be readily increased by several means; including but not limited to, multiple rounds of amplification; the combination of limited cycle PCR and in vitro transcription IVT). The detection sensitivity can be increased by hybridization stability, such as increase the length of final amplification products, including one or several nucleotide analogs, such as locked nucleic acids in probes, to which the amplified miRNAs hybridize. Alternatively, a labeled short oligonucleotide sequence can be attached to amplified miRNA, which increases signal strength and detection sensitivity.

The generation of a signature sequence population to the desired target ncRNA/miRNAs/small polynucleotide sequences in the SSAM (signature sequence amplification methodology) technology is fundamentally different from previous methods which attach a variety of sequences of interest, such as a bacteriophage RNA synthesis promoter, to a cDNA copy of mRNA through reverse transcription. Signature sequences are generated in the presence of target miRNA. However, the 'first strand DNA' in the present invention is not a cDNA copy of a RNA molecule. Rather, it is a DNA copy of a DNA molecule. Instead of being a template, miRNA serves as a primer, and a sequence-specific FON is a template for a DNA dependent DNA synthesis. Although a signature sequence includes a target miRNA sequences, a signature sequence is designed to be significantly longer than the target miRNA sequence.

The FONs and the SONs described herein are designed on the basis of confirmed mature miRNA sequences so that they will only amplify and detect mature but not immature pro- or pre- miRNAs when total RNA populations are used as starting samples. Since only mature miRNAs are biologically functional, the present invention has the advantage over many commercially available direct labeling methods in distinguishing functional from nonfunctional miRNAs. For the same reason, the present invention eliminated the need to enrich or purify miRNAs before miRNA detection.

The present invention can also be used effectively to screen for unknown miRNAs/small polynucleotide sequences, e.g., including, but not limited to, any ncRNA or ribosomal RNA (rRNA), transfer RNA (tRNA), small interfering RNA (siRNA), and small hairpin RNA (shRNA), among others. Instead of attaching a known sequence to the 3' of FONs, a random sequence can be attached. The 5' of FONs will have the requisite functional sequences for the downstream processing of DNAs. After the first DNA synthesis step, and clearing the samples of free unbound FONs, the SONs with a desired sequence and length will be added into the sample. The 3' of the SONs will also be comprised of a random sequence and the 5' will contain necessary functional sequences for DNA amplification and cloning. The double stranded DNAs can either be cloned directly or following an amplification step. The clones can be selected by appropriate antibiotic resistance and confirmed by direct sequencing.

A unique feature of the present invention is the stepwise construction of signature sequences. This functionality distinguishes the present technology from all the other methods available currently, where typically all of the oligonucleotide primers required for the detection scheme are added the reaction mixture simultaneously. In contrast, a signature sequence is composed of two distinct oligonucleotide primers (FON and SON) that anneal to the target miRNA (which serves as a primer for DNA synthesis). The experimental design ensures that FON and SON primers only interact with each other in a sample preparation when target miRNAs are present.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 1:
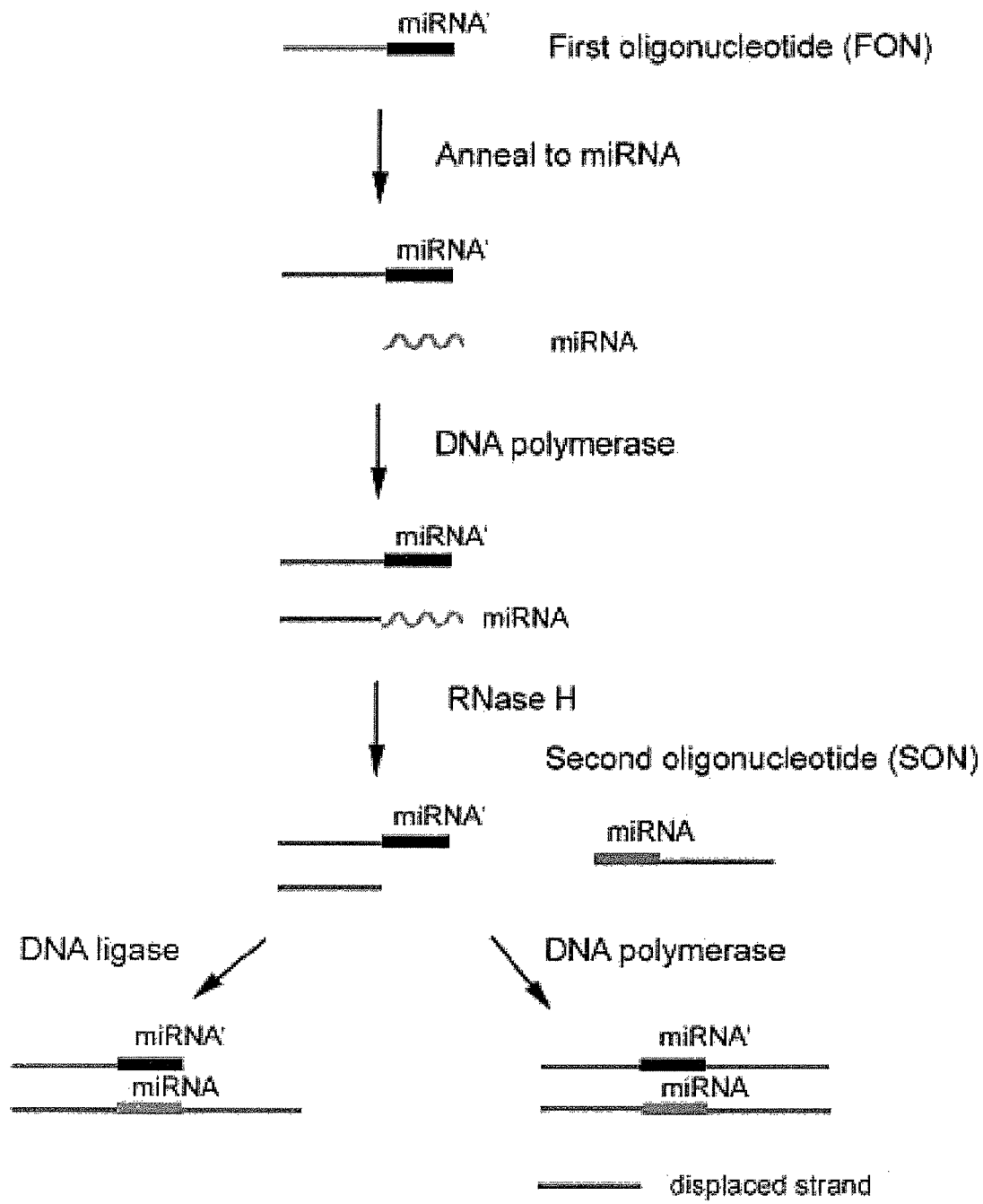
FIG. 1 is a schematic illustrating the signature sequence generation process for amplification of miRNAs/small polynucleotides using SSAM technology.

A "target ncRNA", "target miRNA", or a "potential target miRNA" as used herein, is a ribopolynucleotide comprising a sequence of interest, for which amplification is desired. The target ncRNA and/or miRNA has known sequence, whereas a "potential target miRNA" may be known or not known, in terms of its actual sequence.

A "signature sequence" as used herein, is a representative of a target ncRNA and/or miRNA. A signature sequence is formed by connecting appropriate FONs and SONs in the presence of target ncRNAs and/or miRNAs. The quantity of a signature sequence reflects the quantity of the target miRNA. A signature sequence has all the necessary regions for the downstream designed genetic manipulations, such as PCR, IVT, qPCR, and/or restriction endonuclease digestion, etc. A signature sequence may also be attached with a label, such as a biotin molecule.

A "functional sequence" as used herein, is a sequence, which serves as a RNA synthesis promoter sequence, or a DNA amplification primer attaching sequence, or a restriction enzyme recognition sequence or any other functions for the convenience of genetic manipulations. A functional sequence is usually a short DNA sequence, less than 50 bp in length. Some different functions, such as a RNA synthesis promoter sequence and restriction enzyme cutting sequence requires different sequences; whereas others, such as a RNA synthesis promoter sequence and a PCR primer attaching sequence may share the same DNA sequence.

"Amplification," as used herein, generally refers to the process of producing multiple copies of a desired sequence. A "copy" does not necessarily mean perfect sequence complementarity or identity to the template sequence. For example, copies can include nucleotide analogs such as deoxyinosine. "Multiple copies" mean at least 2 copies. "Amplifying" a sequence may generally refer to making copies of a sequence or its complement, with the understanding that, as stated above, copying does not necessarily mean perfect sequence complementarity or identity with respect to the template sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as locked nucleic acids (LNA's) nucleotides, dideoxycytidine (ddC). If present, modification to the nucleotide structure may be imparted before or after assembly of the polymer. The sequence of nucleotides may be interrupted by non-nucleotide components. A polynucleotide may be further modified after polymerization, such as by conjugation with a labeling component, such as biotinylation.

A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotin-avidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include fluorescent dyes (e.g., fluorescein isothiocyanate, Texas red, rhodamine, green fluorescent protein and the like), radioisotopes (e.g. $^{3}$H, $^{35}$S, $^{32}$P, $^{33}$P, $^{125}$I, or $^{14}$C), enzymes (e.g., LacZ, horseradish peroxidase, alkaline phosphatase), digoxigenin, and colorimetric labels such as colloidal gold or colored glass or plastic (e.g., polystyrene, polypropylene, latex, etc.) beads. Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

A "binding molecule" as used herein, refers to a molecule that is a member of a specific pair of molecules which will bind to each other specifically in a suitable condition. Examples of specific pair of binding molecules include (but not limited to) biotin-avidin, antigen-antibody, and nucleic acid-complementary sequence.

The "type" of dNTP or rNTP, as used herein, refers to the particular base of a nucleotide, namely adenine, cytosine, thymine, uridine, or guanine.

"Oligonucleotide," as used herein, generally refers to short, generally single stranded, generally synthetic polynucleotides that are generally, but not necessarily, less than about 200 nucleotides in length. Oligonucleotides in the invention include the first and second oligonucleotides. The terms "oligonucleotide" and "polynucleotide" are not mutually exclusive. The description above for polynucleotides is equally and fully applicable to oligonucleotides.

A "primer" is generally a nucleotide sequence (i.e., a polynucleotide), generally with a free 3'-OH group, that hybridizes with a template sequence (such as a signature sequence, or a primer extension product) and is capable of promoting polymerization of a polynucleotide complementary to the template. A "primer" can be, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s). An example of a complex is a nucleic acid duplex comprising a first oligonucleotide and a target miRNA extension products or a second oligonucleotide and a target miRNA extension product.

"Denaturing," is dissociation of any hydrogen bond formed within a polynucleotide (such as a first oligonucleotide or a second oligonucleotide). "Denaturation of" a complex (such as a FON extension product and a SON extension product) refers to dissociation of two hybridized polynucleotide sequences in the complex. The dissociation may involve a portion or the whole of each polynucleotide. Thus, denaturation of a complex comprising two polynucleotides can result in complete dissociation (thus generating two single stranded polynucleotides), or partial dissociation (thus generating a mixture of single stranded and hybridized portions in a previously double stranded region of the complex).

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence.

A "reaction mixture" is an assemblage of components, which, under suitable conditions, react to form a complex (which may be an intermediate) and/or a product(s).

"Appropriate conditions" are conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

"Microarray" and "array," as used interchangeably herein, comprise a surface with an array, preferably ordered array, of putative binding (e.g., by hybridization) sites for a biological sample (target). In a preferred embodiment, a microarray refers to an assembly of distinct polynucleotide or oligonucleotide probes immobilized at defined positions on a substrate. Arrays are formed on substrates fabricated with materials such as paper, glass, ceramic, plastic (e.g., polypropylene, nylon, polystyrene), polyacrylamide, nitrocellulose, silicon or other metals, optical fiber or any other suitable solid or semisolid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (U.S. Pat. Nos. 5,578,832, 5,556,752, and 5,510,270); (ii) spotting/printing at medium to low-density (e.g., cDNA probes) on glass, nylon, or nitrocellulose; (iii) by masking and (iv) by dot-blotting on a nylon or nitrocellulose hybridization membrane. Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide or moieties attached to the 5' most nucleotide of the same polynucleotide or oligonucleotide.

The term "arbitrary sequence" refers as any defined or pre-selected deoxyribonucleotide, ribonucleotide or mixed deoxyribo/ribonucleotide sequence which contains a particular sequence of natural or modified nucleotides.

The term "random sequence" is defined as deoxyribonucleotide, ribonucleotide or mixed deoxyribo/ribonucleotide sequence which contains in each nucleotide position any natural or modified nucleotide.

As used herein, the term "RNA/DNA hybrid" refers to a product after first DNA synthesis catalyzed by DNA polymerase. In a preferred embodiment "RNA/DNA hybrid" comprises a first oligonucleotide, a target miRNA and a target miRNA extension product.

Two sequences are said to be "complementary" to one another if they are capable of hybridizing to one another to form antiparallel, double-stranded nucleic acid structure.

The term "solid support" refers to any known substrate which can be used for the immobilization of a binding ligand or oligonucleotide/polynucleotide sequences by any known method.

The term "nucleotide analog" refers to a nucleotide which is not typically found in the in DNA or RNA and possesses some additional features which can improve efficiency of generating the signature sequences or detection of target molecules. For example, suitable nucleotide analogs include modification in the base or sugar-phosphate backbone, like peptide nucleic acid, inosin, 5-nitroindole deoxyribofuranosyl, 5-methyldeoxycytosine, and 5,6-dihydro-5,6-dihydroxydeoxythymidine. Other nucleotide analogs will be evident to those skilled in the art.

The invention provides methods, compositions, and kits for the amplification of small polynucleotide, especially ncRNAs including, but not limited to miRNAs from nanogram quantities of total RNA or enriched small RNAs, as well as applications of the amplification methods. The compositions and methods herein employ signature sequence generation to the population of target miRNAs and/or small polynucleotide sequences in biological samples.

In one aspect, the invention provides methods to generate a signature sequence, said method comprising the steps of (a) hybridizing a target miRNA/small polynucleotide sequence to a first oligonucleotide (FON); (b) extending the target miRNA/small polynucleotide sequence hybridized to FON with a DNA polymerase to generate a RNA/DNA double-stranded hybrid molecule; (c) cleaving the target miRNA/small polynucleotide sequence in the complex of step (b) which generates a double stranded DNA molecule with 3' overhang; (d) hybridizing a second oligonucleotide (SON) to the product of step (c). The SONs have 3' sequences complimentary to the 3' overhangs of the double stranded DNA molecules generated in step (c).

Steps (a) to (d) are followed by alternative steps (e1) or (e2). Step (e1) involves ligating the SON with a DNA ligase to the DNA fragments of the double-stranded DNA molecule of step (d), whereby generating a partially double stranded signature sequence to the target miRNA. Step (e2) involves filling in the overhangs of FON and the SON annealed to each other with a DNA dependent DNA polymerase to generate a double stranded signature sequence.

In another aspect, the invention provides methods to generate a plurality of signature sequences comprising the steps of: (a) incubating a biological sample with a desired pool of the first oligonucleotides (FONs) to hybridize the pool of target miRNAs in the said sample; (b) extending the target miRNAs hybridized to the FONs with a DNA polymerase to generate a pool of double stranded DNA/RNA hybrid molecules; (c) cleaving the miRNAs in the double stranded DNA/RNA hybrid molecules of step (b) which generates a pool of double stranded DNA molecules with 3' overhangs; and (d) incubating the sample generated at step (c) a pool of the second oligonucleotide (SONs). The SONs have 3' sequences complementary to the 3' overhangs of the double stranded DNA molecules generated in step (c).

The steps (a) to (d) are followed by alternative steps (e1) or (e2). Step (e1) involves ligating SONs with a DNA ligase to the DNA fragments of the double-stranded DNA molecules of step (d), thereby generating a pool of partially double stranded signature sequences to the target miRNAs. Step (e2) involves filling in the overhangs of the FONs and the annealed SONs with a DNA dependent DNA polymerase to generate a pool of double stranded signature sequences.

For the first step DNA synthesis, the FON and/or FONs are added into a sample containing or potentially containing at least one target miRNA/small polynucleotide sequence. The said FONs and the said target miRNAs/small polynucleotide sequences will in an appropriate condition anneal to each other at their 3' ends with extruding 5' ends of the FONs. The target miRNAs that anneal to appropriate FONs will then act as DNA synthesis primers, whereas the extruding 5' end of a FONs will act as DNA synthesis templates. In the presence of a proper DNA polymerase and other component for DNA synthesis, double stranded DNA/RNA hybrids are formed, as seen in FIG. 1.

Referring to FIG. 1, the schematic depicts the presence of a target miRNA, and a FON sequence complementary to the target miRNA. A double stranded or partial double stranded RNA/DNA hybrid is generated using DNA polymerase. Following RNase treatment, a SON containing the miRNA sequence plus a portion of signature sequence is added to the reaction mixture. DNA ligase can be added to ligate the SON to the double stranded/partial double stranded first DNA synthesis product to form the signature sequence. Alternatively, DNA polymerase can be added to create a double stranded miRNA signature sequence along with the displaced strand (displaced by the extended SON). Importantly, the quantities of any double stranded DNA/RNA hybrid product are directly proportional to the target miRNAs present in the sample.

After the first DNA synthesis reaction, the said target miRNAs/small polynucleotide sequences in formed DNA/RNA hybrid molecules are digested with an RNA endonuclease, such as RNase H. A pool of SONs is then added to the sample. The DNA copy of target miRNA sequence included in a SON is necessary, through which a SON anneals to a corresponding FON. In the presence of a DNA ligase, a SON annealed to a corresponding FON ligates to the DNA fragment generated in the first strand DNA synthesis and left after the enzymatic digestion of the target miRNA. Alternatively, the 5' end overhangs of a FON and a SON annealed together can be filled by a DNA polymerase using annealed both 3' end as primers.

Figure 2:
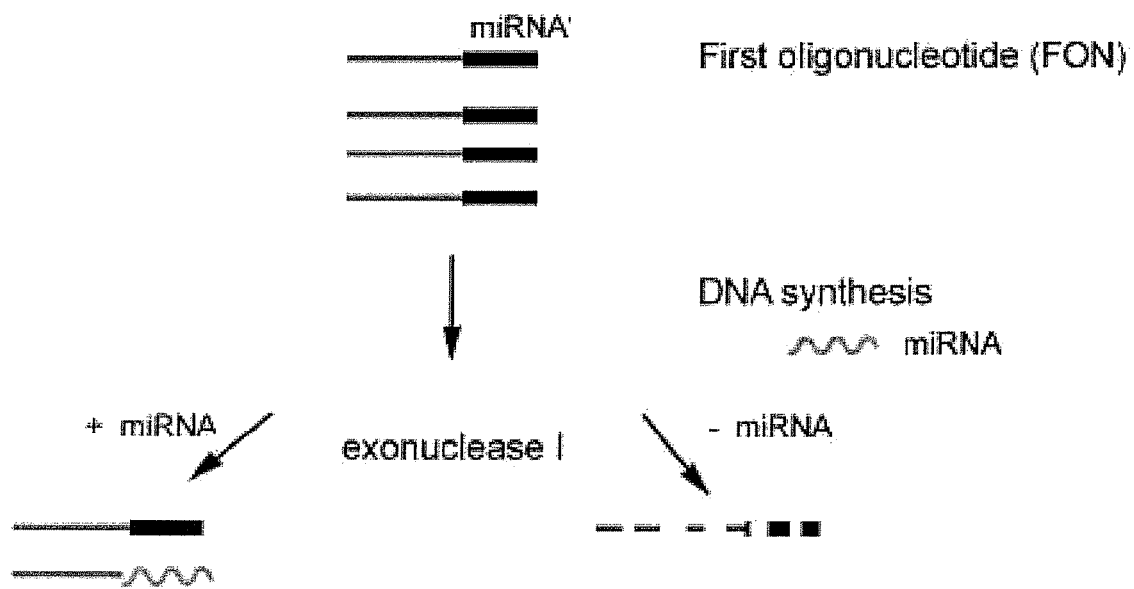
FIG. 2 is a schematic illustrating the clearance of free single stranded FON with enzymatic digestion by exonuclease I before the addition of SONs.

In some aspects, the sample may be cleared of the free FONs before the SONs are added. The FONs can be removed by any methods known in the art or the methods described herein, comprising: (a) incubating a RNA sample with FONs to hybridize target miRNAs/small polynucleotide sequences; (b) extending the target miRNAs/small polynucleotide sequences hybridized to FONs with a DNA polymerase to generate a double-stranded RNA/DNA hybrid molecules, which is followed by either step (c) or (d) or (e), where step (c) involves enzymatically digesting the single stranded free FONs with exonuclease I, as seen in FIG. 2, step (d) involves the use of a restriction nuclease digestion site and a binding molecule such as biotin are included at the 5' end of FONs, and step (e) involves displacement of the reverse complementary strand of double-stranded FON by the first step DNA synthesis. Referring to FIG. 2, double stranded RNA/DNA hybrid molecules are protected from digestion and can be processed for downstream amplification.

Figure 3:
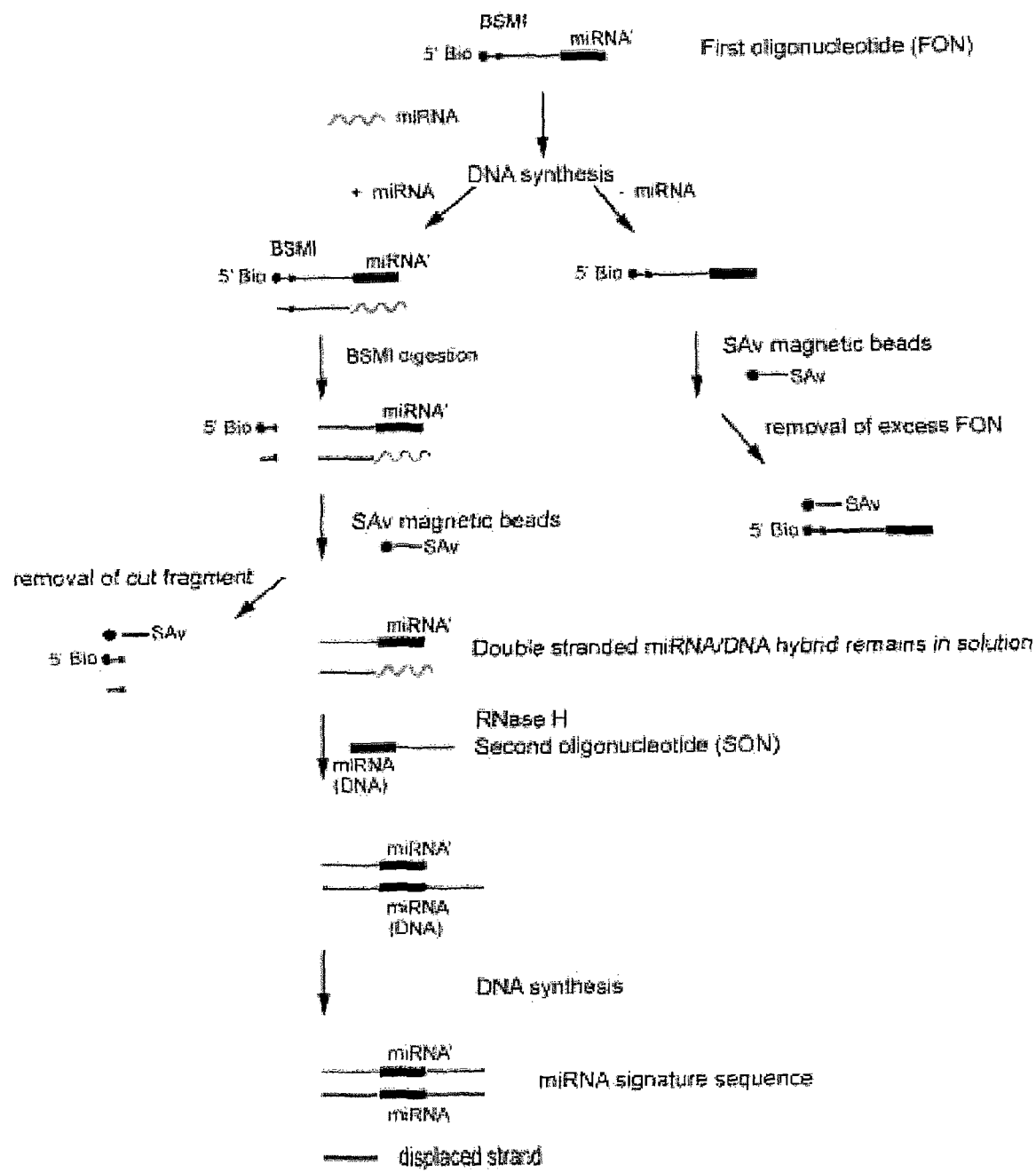
FIG. 3 is a schematic illustrating the clearance of single stranded free FONs via restriction enzyme digestion before the addition of SONs.

After the formation of the double-stranded RNA/DNA hybrid molecules, the single-stranded free FONs can be removed by digesting the double stranded RNA/DNA hybrid molecules with an appropriate restrictive endonuclease, followed by binding undigested single stranded free FON through a binding group, such as biotin to an avidin molecule immobilized on a solid or semi-solid substrate; and separate the solid substrate from the sample whereby the free FONs are removed from the sample, as seen in FIG. 3. Referring to FIG. 3, all the FONs have a biotin moiety and a restriction enzyme BSMI recognition sequence at the 5' end. In the presence of the target miRNAs/small polynucleotide sequences, the BSMI recognition site becomes double stranded after first step DNA synthesis and will be cut by BSMI into a small DNA fragment and a main body of RNA/DNA hybrid molecule. By contrast, in the absence of the target miRNAs, the BSMI sequence will remain single stranded and will not be cleaved by BSMI. The biotinylated single stranded FONs and 5' small fragments of cut from the double stranded RNA/DNA signature sequence hybrid are removed out of the solution by streptavidin (SAv) conjugated magnetic beads, leaving the intact double stranded miRNA/signature sequence hybrid in solution for downstream applications. It should be noted that the FONs that formed the RNA/DNA hybrid molecules in the presence of the target miRNA/small polynucleotide sequence will remain in the sample except the small double stranded DNA fragments cleaved off by a restriction enzyme. The quantities of the remaining FONs are parallel to the quantities of the target miRNAs present in the samples.

Figure 4:
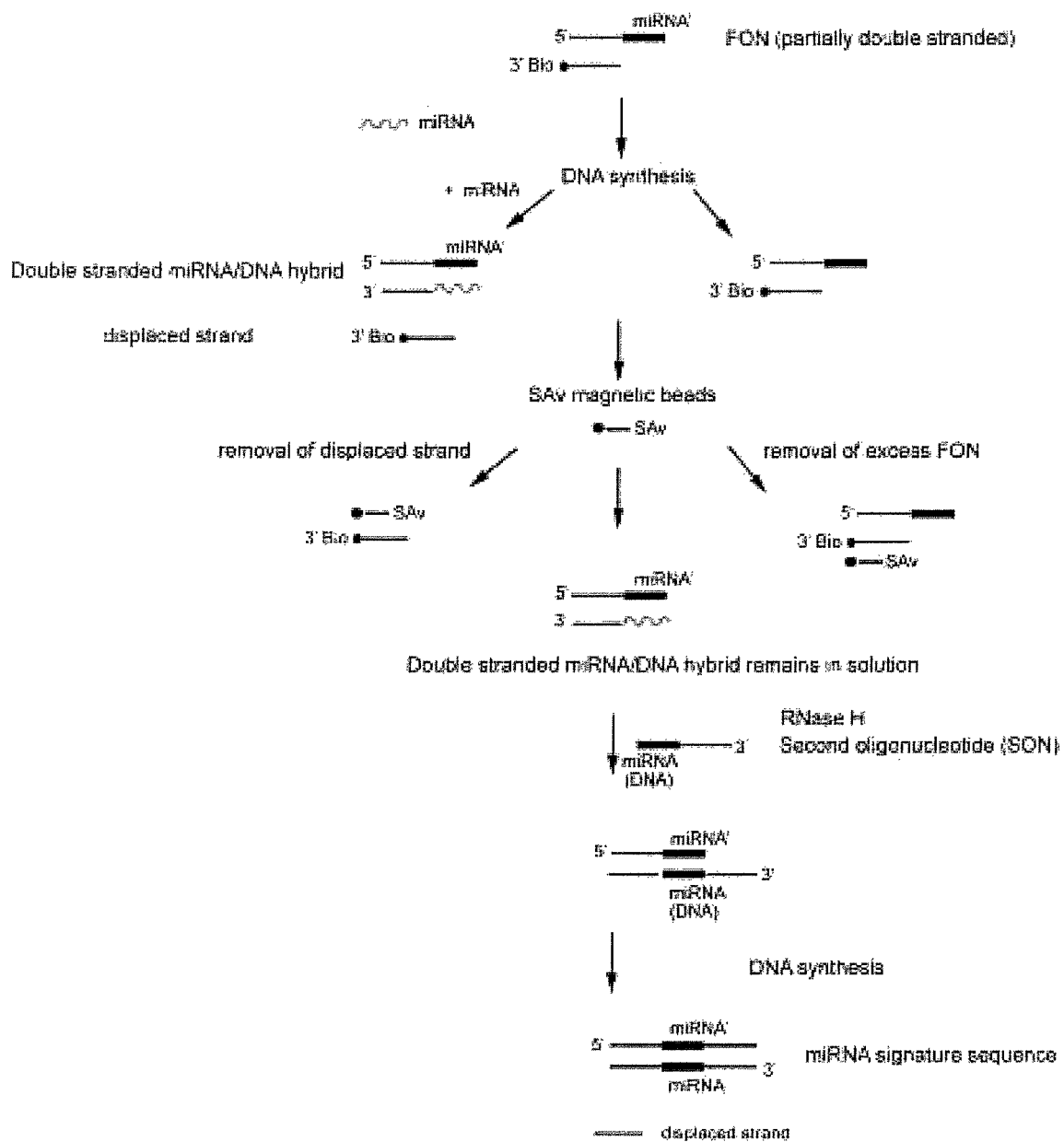
FIG. 4 is a schematic illustrating clearance of free FONs through the mechanism of strand displacement before the addition of SONs.

With respect to step (e) of hybridizing FONs with a reverse complementary sequence, the said sequence is complementary to 5' end of the FONs and has a binding molecule, such as biotin at its 3' end. This partially double-stranded FONs anneal to target miRNAs/small polynucleotides in a sample and the reverse complementary sequence is released by strand displacement in DNA synthesis. After the first DNA strand synthesis, any free partially double stranded FONs and displaced reverse complementary sequence can be cleared out of the solution by SAv conjugated magnetic beads, leaving the intact double stranded miRNA/signature sequence hybrid molecules in solution. It should be noted that the FONs that formed the RNA/DNA hybrid molecules in the presence of the target miRNA/small polynucleotide sequence will remain in the sample because the biotin conjugated reverse complementary sequence is displaced in the presence of the target miRNA/small polynucleotide sequence whereas free partially double stranded FONs and displaced reverse complementary sequence will bind to immobilized SAv and cleared from the sample, as seen in FIG. 4. Referring to FIG. 4, the FONs are partially double stranded. The shorter strands do not hybridize to miRNA annealing sequences and are biotin labeled at 3' end. In the presence of target miRNAs, DNA synthesis will displace the shorter strand with synthesized strands and the displaced strands are later removed from the solution by SAv conjugated beads. The double stranded RNA/DNA hybrids formed in the presence of target miRNA will remain in the solution. In the absence of target miRNA, no DNA synthesis will occur, and the partial double stranded FONs will be removed from the solution by SAv conjugated magnetic beads that bind to the 3' biotin moiety.

The application of other binding molecules, which binds with sufficient affinity to a partner are also in the scope of the invention. The examples of such molecules include, but not limited to, an antigen-antibody, an oligonucleotide-complementary oligonucleotide sequence, a biotin-avidin and an enzyme-substrate.

A SON will be added into the reaction mixture after the free FON is cleared. The said SON will hybridize to the 3' end of RNA/DNA hybrid molecule after the digestion of miRNA in the molecule. The signature sequence is generated by either ligation or a DNA synthesis step as shown in FIG. 1.

Figure 5:
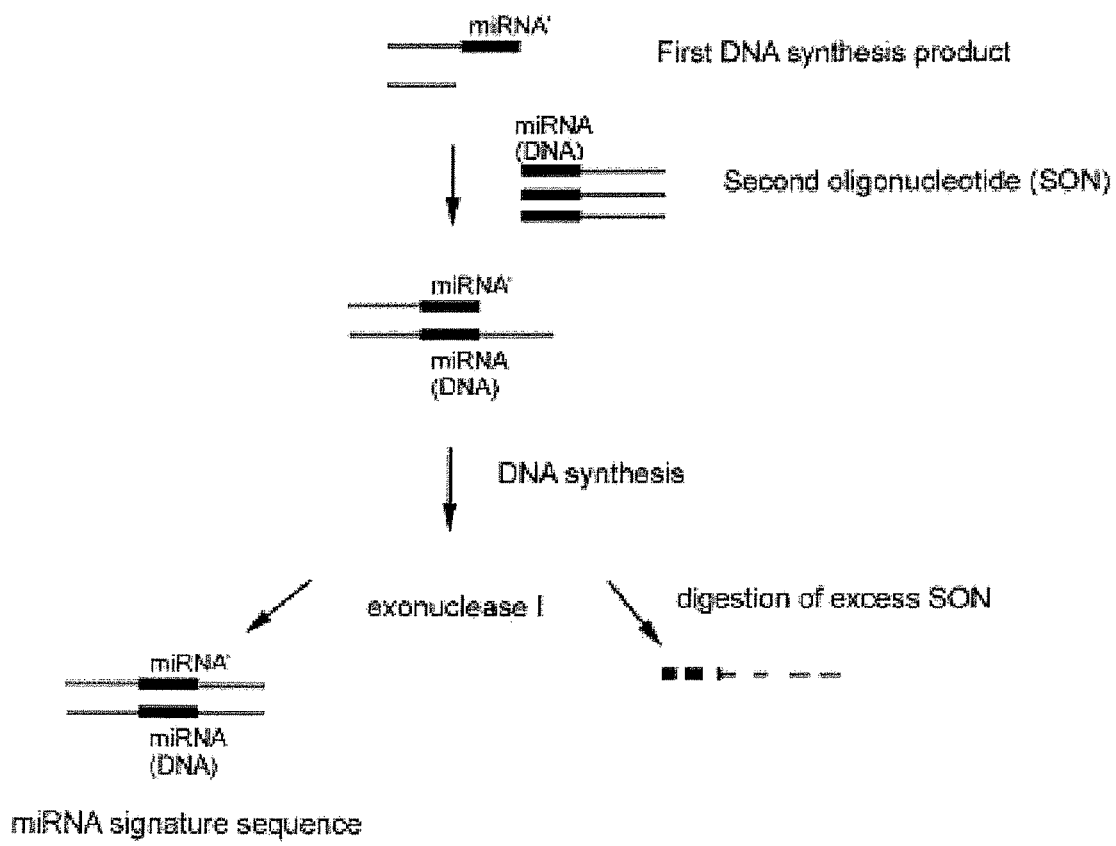
FIG. 5 is a schematic illustrating the clearance of free single stranded SONs after the second DNA synthesis through digestion of exonuclease I. The signature sequences formed after the second DNA synthesis are double stranded and resistant to exonuclease I digestion.
Figure 6:
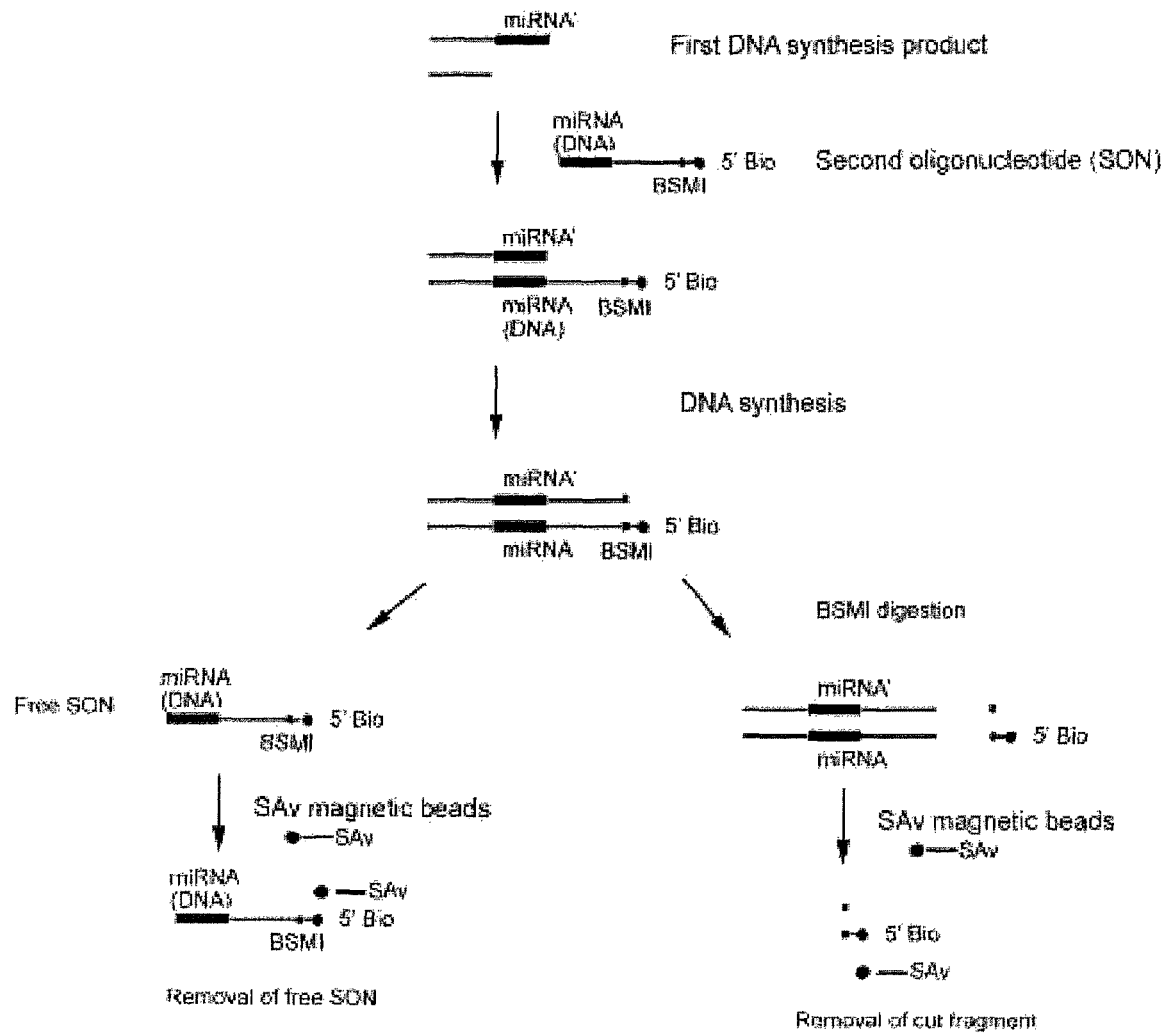
FIG. 6 is a schematic illustrating the clearance of free single stranded SONs after the second DNA synthesis through BSMI restriction digestion and streptavidin (SAv) magnetic beads.
Figure 7:
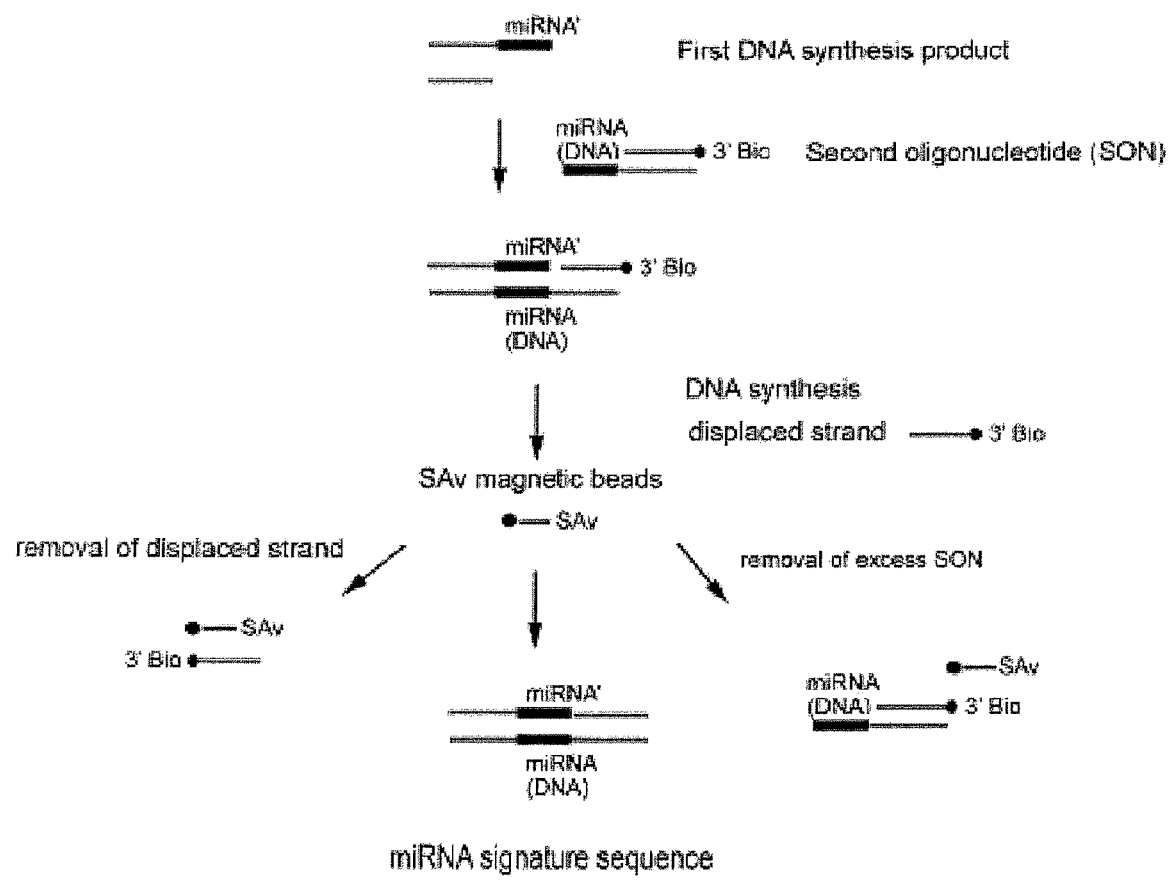
FIG. 7 is a schematic illustrating the clearance of free SONs after the second DNA synthesis through the mechanism of strand displacement.

As with the clearance of FON before the following steps described herein, the samples can also be cleared of the SONs before proceeding to downstream amplification and subsequent functional genomics applications as shown in FIGS. 5-7.

The SONs can be removed by any methods known in the art or the methods described herein, comprising: (a) adding to the sample containing RNA/DNA hybrid molecules SONs to hybridize each other at 3' ends; (b) extending both 3' ends with a DNA polymerase to generate a double-stranded signature sequence, which is followed by either step (c) or (d) or (e), where step (c) involves enzymatically digesting the single stranded free SONs with exonuclease I, as seen in FIG. 5, step (d) involves the use of a restrictive endonuclease digestion and a binding molecule such as biotin at the 5' end of SONs, and step (e) involves displacement of the antisense strand of a partially double-stranded FON by the second step DNA synthesis. Referring to FIG. 5, double stranded RNA/DNA hybrid molecules are protected from the exonuclease digestion and can be processed for downstream amplification.

After the formation of the double-stranded signature sequence, a restriction endonuclease such as BSMI will cut off a small fragment at the end whereas the single-stranded free SONs will stay intact. The small fragment and the intact free single stranded SONs can be removed by interaction with a binding group, such as biotin to an streptavidin molecule immobilized on a solid or semi-solid substrate; and separate the solid substrate from the sample whereby the free SONs are removed from the sample, as seen in FIG. 6.

Referring to FIG. 6, all the SONs have a biotin moiety and a restriction enzyme BSMI recognition sequence at the 5' end. In the presence of the RNA/DNA hybrid molecules, the BSMI recognition site becomes double stranded after second step DNA synthesis and will be cut by BSMI into a small DNA fragment and a main body of signature sequence. By contrast, in the absence of the RNA/DNA hybrid molecules, the BSMI sequence will remain single stranded and will not be cleaved by BSMI. The biotinylated single stranded SONs and 5' small fragments cut from the doubled stranded signature sequence are removed out of the solution by SAv conjugated magnetic beads, leaving the main body of functional double stranded signature sequence in solution for downstream applications.

Step (e) is illustrated in FIG. 7. The SON is partially double stranded, and the sense strand has an overhang at 3' end. The antisense strand has a binding moiety, such as biotin molecule, at the 3' end. This partially double-stranded SON anneals to the RNA/DNA hybrid molecule in the sample, and the antisense strand is released by strand displacement in DNA synthesis. After the second DNA strand synthesis, any free partially double stranded SONs and displaced antisense strands can be cleared using the same method as in step (d). It should be noted that the SONs that formed the double stranded signature sequences would remain in the sample because the biotin conjugated antisense strand is displaced and no longer binding to the sense strand. The free partially double stranded FONs and the displaced antisense strand will then bind to SAv conjugated beads and be cleared from the solution.

Referring to FIG. 7, the SONs are partially double stranded. The shorter strands are antisense strands, which do not hybridize to RNA/DNA hybrid molecules and are biotin labeled at 3' end. In the presence of RNA/DNA hybrid molecules, DNA synthesis will displace the antisense strand with synthesized DNA sequence and the displaced antisense strands are later removed from the solution by SAv conjugated beads. The double stranded signature sequences formed in the presence of target miRNA will remain in the solution. In the absence of RNA/DNA hybrid, no DNA synthesis will occur, and the free partial double stranded SONs will be removed from the solution by SAv conjugated magnetic beads that bind to the 3' biotin moiety.

Figure 8:
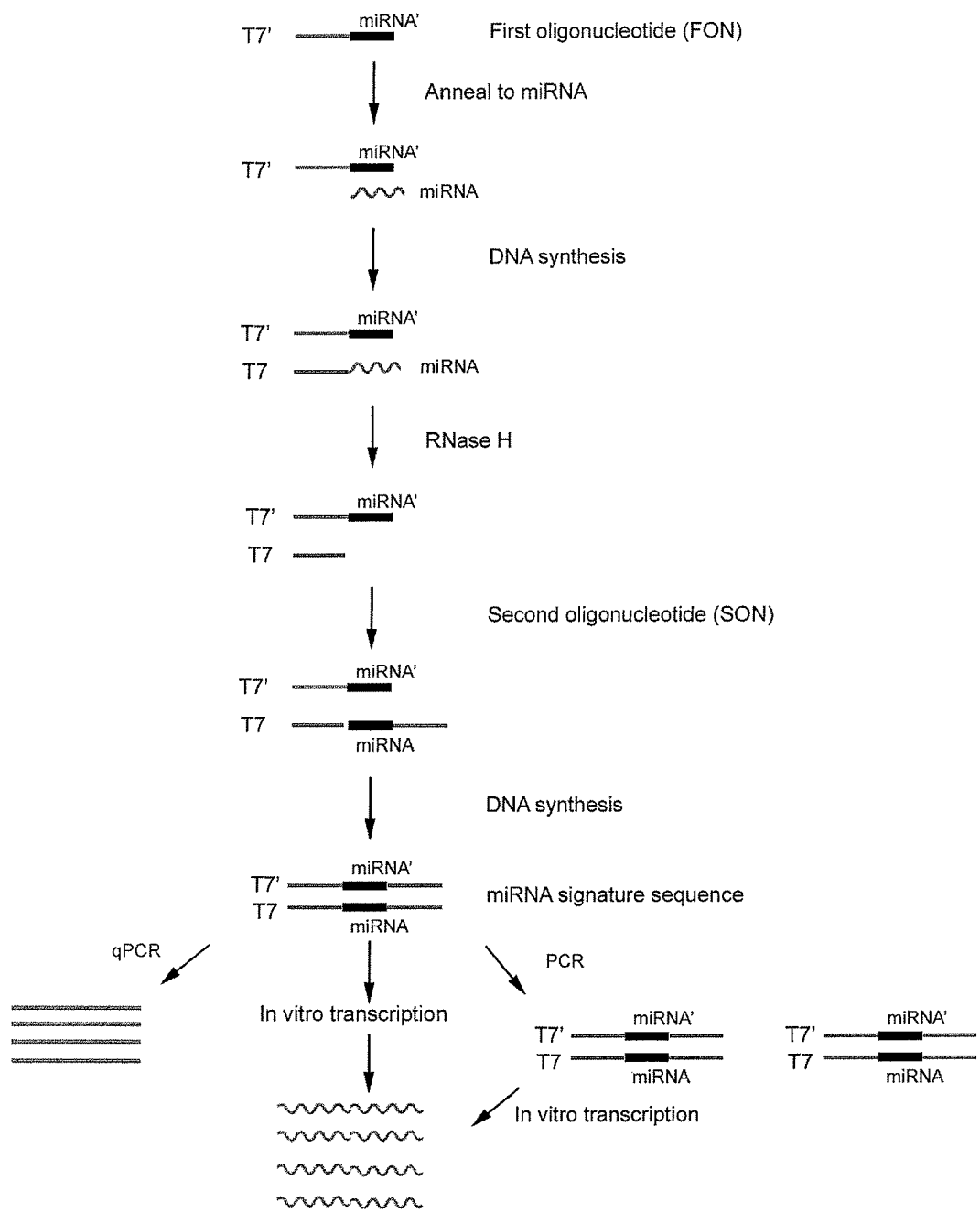
FIG. 8 is a schematic illustrating the mechanisms of amplifying signature sequences for the SSAM technology.

In one aspect, the invention provides methods of generating multiple copies (amplification) of the target miRNAs, the said method comprises generating the signature sequences of target miRNAs, followed by amplification through PCR, qPCR, or IVT, and the combination of any above method, as seen in FIG. 8. In another aspect, the amplification products of the target miRNAs are DNA copies of whole or part of the signature sequences, such as when signature sequences are amplified with PCR or qPCR. Yet in another aspect, the amplification products of the target miRNAs are RNA copies of whole or part of signature sequences, such as when signature sequences are amplified with IVT, or PCR followed by IVT.

Also within the scope of the present invention is a method for search unknown miRNAs/small polynucleotide sequences. The method generates a plurality of unknown signature sequences and comprises the following steps: (a) incubating a RNA sample with a plurality of the FONs with random sequences at the 3' end to hybridize the pool of unknown miRNAs/small polynucleotide sequences in the RNA; (b) extending the unknown potential miRNAs hybridized to the FONs with a DNA polymerase to generate a plurality of double stranded DNA/RNA hybrid molecules; (c) cleaving the miRNAs with a ribonuclease in the double stranded RNA/DNA hybrid molecules of step (b) which generates a plurality of double stranded DNA molecules with 3' overhangs; (d) incubating the sample generated at step (c) a plurality of the SONs. The SONs have random 3' sequences that will bind to the double stranded DNA molecules generated in step (c); and (e) extending 3' ends of FONs and SONs with a DNA polymerase, whereby to generate a double stranded signature sequences with unknown potential miRNAs.

Various embodiments described herein can be used to clear the free FONs and free SONs before proceeding to the next step.

Various embodiments of methods can be used to determine the presence/absence and sequence of the captured potential miRNAs. In some of these embodiments, the double stranded signature sequences generated in step (e) can be directly cloned into a cloning vector. In other embodiments, the double stranded signature sequence generated in step (e) can be first amplified via PCR before cloned into a cloning vector. The clones containing the unknown potential ncRNAs/miRNAs/small polynucleotide sequences will be first screened for the presence of appropriate insert sizes and then confirmed by definitive sequencing.

In a preferred embodiment, the random sequences at 3' of a FON or/and a SON described herein is at least one nucleotide in length and preferably 6-10 nucleotides in length.

In one aspect, the invention provides methods to generate labeled polynucleotide products (generally DNA or RNA products). In some embodiments of methods for generating labeled DNA products, at least on type of dNTP used is a labeled dNTP. In some embodiments of methods for generation labeled RNA products, at least on type of rNTP used is a labeled rNTP.

Also within the scope of this invention is the detection of the said miRNA/small polynucleotide signature sequence population amplification product.

In one aspect, the invention provides a method of characterizing an miRNA sequence of interest, comprising: (a) amplifying a target miRNA by a method described herein to generate labeled products; and (b) analyzing the labeled products. In some embodiments, the step of analyzing miRNA products comprises determining amount of said products, whereby the amount of the target miRNA present in a sample is quantified. The oligonucleotide products can be analyzed by, for example, contacting them with at least on probe. In some embodiments, at least one probe is provided as a microarray. The microarray comprises at least one probe immobilized on a solid or semi-solid substrate fabricated from a material selected from the group consisting of paper, glass, ceramic, plastic, polypropylene, nylon, polyacrylamide, nitrocellulose, silicon, and optical fiber. An amplification product can be immobilized on the solid or semi-solid substrate in a two-dimensional configuration or a three-dimensional configuration comprising pins, rods, fibers, tapes, threads, beads, particles, microtiter wells, capillaries, and cylinders.

In another aspect, the invention provides methods of producing a nucleic acid immobilized to a substrate (which includes methods of producing a microarray), comprising (a) amplifying a predetermined portion of a target miRNA signature sequence by any of a DNA amplification method known in the field of art, such as PCR; and (b) immobilizing the amplification products on a substrate. The amplification products can be labeled or unlabeled. In other aspects, the invention provides methods of producing a microarray, comprising: (a) amplifying a predetermined portion of target miRNA signature sequence by a DNA amplification method known in the field of art, such as PCR; and (b) immobilizing the amplification products on a substrate (which can be solid or semi-solid). In some embodiments, microarrays are produced by immobilizing amplification products onto appropriate substrates. The microarray can comprise at least one amplification product immobilized on a solid or semi-solid substrate fabricated from a material selected from the group consisting of paper, glass, ceramic, plastic, polypropylene, nylon, polyacrylamide, nitrocellulose, silicon, and optical fiber. An amplification product can be immobilized on the solid or semi-solid substrate in a two-dimensional configuration or a three-dimensional configuration comprising pins, rods, fibers, tapes, threads, beads, particles, microtiter wells, capillaries, and cylinders.

In another embodiment, the invention provides methods for characterizing (for example, detection and/or quantifying and/or determining presence or absence of) a target miRNA/small polynucleotide sequence comprising: (a) amplifying a target miRNA by any of the methods described herein; and (b) analyzing the amplification products. Step (b) of analyzing the amplification products can be performed by any method known in the art or described herein, for example by detecting and/or quantifying and/or determining present or absence of amplification products that are hybridized to a probe. These amplification products may or may not be labeled.

Any of the methods of the invention can be used to generate oligonucleotide (either riboligonucleotide or deoxyriboligonucleotide) products that are labeled by incorporating labeled nucleotides into appropriate step(s) of the methods.

As will be clear to one skilled in the art, reference to production of copies of an RNA or DNA sequence of interest or copies of a polynucleotide sequence complementary to an RNA or DNA sequence of interest refers to products that may contain, comprise or consist of such sequences. As is evident to one skilled in the art, aspects that refer to combining and incubating the resultant mixture also encompasses method embodiments which comprise incubating the various mixtures (in various combinations and/or subcombinations) so that the desired products are formed. It is understood that any combination of these incubation steps, and any single incubation step, to the extent that the incubation is performed as part of any of the methods described herein, fall within the scope of the invention. It is also understood that methods that comprise one or more incubation steps do not require a separate combination step, as such combinations are implicit in incubating the reaction mixture(s).

Various embodiments of the oligonucleotides are used in the methods of the invention. For example, in some embodiments, a FON comprises a 5' portion that will not hybridize (under a given set of conditions) to a target RNA. In some of these embodiments, the 5' portion comprises a sequence the complement of which is capable of hybridization by a RNA synthesis promoter polynucleotide under a given set of conditions. In one example, the presence of said 5' portion in the first oligonucleotide results in generation of a second oligonucleotide extension product that is hybridizable (under a given set of conditions) by a RNA synthesis promoter polynucleotide. In some embodiments, a FON contains at its 3' end a DNA sequence that is complementary to a portion or a whole sequence of a target miRNA. In some other embodiments, 5' end of a FON contains DNA sequences of varies functions, such as RNA polymerase promoters, or/and restriction endonuclease digestion sites, and DNA synthesis primer attaching sites, among others. In a pool of FONs, each FON has a different 3' end complementary to a unique target miRNA/small polynucleotide sequence, all FONs have the same 5' end, such as RNA polymerase promoters, or/and restriction endonuclease digestion sites, DNA synthesis primer attaching sites, among others. In some aspects, any arbitrary/and or random sequence can also be included in a FON. In yet other embodiments, each SON has a specific, unique sequence and contains at least a DNA copy of a portion or whole sequence of one target miRNA/small polynucleotide sequence at its 3' end. In some embodiments, other sequences of various functions, such as RNA polymerase promoters, or/and restriction endonuclease cutting sites, DNA synthesis primer attaching sites, among others will also be included in a SON sequence. In yet another aspect of the invention, plural DNA copies of partial or whole sequence of a target miRNA can be included in a SON. In further aspects of the invention, any arbitrary and/or random sequence can also be included in a SON.

The enzymes which may be used in the methods and compositions are described herein. For example, many different DNA polymerases, such as E. coli DNA polymerase I, large fragment of E. coli DNA polymerase I, Taq polymerase, T7 DNA polymerase, T4 DNA polymerase, or reverse transcriptase could be used for the first DNA synthesis step. T4 ligase, E. coli ligase, Taq ligase, 90N ligase can all be used to ligate a SON to DNA extension of the target miRNA. The enzyme that cleaves the RNA may be RNase H. A DNA polymerase may comprise both RNA-dependent and DNA-dependent DNA polymerase enzyme activities. A DNA-dependent DNA polymerase and an enzyme that cleaves RNA may be the same enzyme. A DNA-dependent DNA polymerase, an RNA-dependent DNA polymerase, and the enzyme that cleaves RNA can also be the same enzyme.

The methods are applicable to amplifying any RNA target, especially small RNAs, such as miRNA, mRNA, ribosomal RNA (rRNA), transfer RNA (tRNA), small interfering RNA (siRNA), and small hairpin RNA (shRNA). One or more steps may be combined and/or performed sequentially, often in any order, as long as the requisite product(s) are capable of being formed. It is also evident, and is described herein, that the invention encompasses methods in which various oligonucleotides may be applied.

The invention also provides methods which employ (usually, analyze) the products of the amplification methods of the invention, such as sequencing, determining presence or absence of a sequence of interest; gene expression profiling; subtractive hybridization; preparation of a subtractive hybridization probe; differential amplification; preparation of small RNA libraries (including differential expression libraries); generation of siRNA and/or shRNA probes; preparation of an immobilized nucleic acid (which can be a nucleic acid immobilized on a microarray), and characterizing (including detecting and/or quantifying) amplified nucleic acid products generated by the methods of the invention.

The invention also provides compositions, kits, complexes, reaction mixtures and systems comprising various components (and various combinations of the components) used in the amplification methods described herein. The compositions may be any component(s), reaction mixture and/or intermediate described herein, as well as any combination thereof.

In some embodiments, the invention provides a composition comprising: (a) FONs; (b) SONs. In some of these embodiments, the 3' end of a FON comprises a short deoxynucleotide complementary to a portion or entire target miRNA, which hybridizes to the target miRNA. The said deoxynucleotide is at least one deoxynucleotide in length but not longer than the length of the target miRNA. The preferred length of said deoxynucleotide is between 6 to the full length of the target miRNA/small polynucleotide sequence. In other embodiment, a FON has a random 3' end sequence which hybridizes to the potential unknown miRNAs/small polynucleotide sequences in a sample. The random sequence is at least one nt in length; the preferred length of the random sequences is 6-15 nts in length.

In some embodiments, the FON comprises a RNA synthesis promoter, an arbitrary sequence to anneal a DNA synthesis primer, or a restriction endonuclease digestion site.

In some embodiments, the RNA promoter is a bacteriophage RNA synthesis promoter, a eukaryotic RNA synthesis promoter, or a recombinant promoter. The said bacteriophage RNA synthesis promoter is a T7 RNA synthesis promoter, a T3 synthesis promoter, or a Sp6 RNA synthesis promoter.

In other embodiments, at least one nucleotide at the 3' end of a FON is a modified nucleotide, which prohibits the elongation of the FON. Examples of such modified nucleotides are dedeoxynucleotide and inverted deoxynucleotide.

In a preferred embodiment, 3' end of a SON comprises of at least one copy of deoxynucleotide sequence of a portion or whole target miRNA. The said deoxynucleotide sequence of the SON binds to the 3' of the appropriate FON present in the sample. The said deoxynucleotide sequence is at least one nt in length but not longer than the length of target miRNA/small polynucleotide sequence. The preferred length of said deoxyoligonucleotide is between 8 to the full length of the target miRNA/small polynucleotide sequence.

In other embodiment, a SON has a random 3' end sequence which hybridizes to the potential unknown miRNAs in a sample. The random sequence is at least one nucleotide in length; the preferred length of the random sequences is 6-15 nucleotides in length.

In a preferred embodiment, the said SON comprises plural deoxynucleotide copies of the target miRNA/small polynucleotide sequence. The deoxynucleotide copies of a miRNA/small polynucleotide sequence can be complete or incomplete. The deoxynucleotide copies are at least one nucleotide in length but not longer than the length of target miRNA/small polynucleotide sequence.

In some embodiments, the said SON comprises a RNA synthesis promoter, an arbitrary sequence to anneal a DNA synthesis primer, or a restriction endonuclease digestion site.

The RNA promoter is a bacteriophage RNA synthesis promoter, a eukaryotic RNA synthesis promoter, or a recombinant promoter. The said bacteriophage RNA synthesis promoter is a T7 RNA synthesis promoter, a T3 synthesis promoter, or an Sp6 RNA synthesis promoter.

The invention also provides compositions comprising (a) a FON hybridizable to target miRNA; (b) a SON hybridizable to a FON extension product. In some embodiments, the composition further comprises one or more of the following: DNA-dependent DNA polymerase, RNA-dependent DNA polymerase, and an agent (generally an enzyme) that cleaves RNA from an RNA/DNA hybrid molecule. In some other embodiment, the composition further comprises one or more of the following: an agent (generally a enzyme) to cleave the single stranded DNA, a restriction enzyme, and a solid support attached molecule, such as SAv.

The invention also provides compositions comprising the amplification products described herein. Accordingly, the invention provides a population of RNA molecules which are copies of a signature sequence, which are produced by any of the methods described herein. The invention also provides a population of polynucleotides (generally DNA) molecules, which are produced by any of the methods described herein.

In another aspect, the invention provides compositions comprising any of the complexes (which are generally considered as intermediates with respect to the final amplification products) described herein. For example, the invention provides compositions comprising a complex of (a) a FON extension product; and (b) a target miRNA strand. In yet another aspect, the invention provides compositions comprising a complex of: (a) a FON extension product; and (b) a SON extension product.

In another aspect, the invention includes any one or more products (including intermediates) and compositions comprising the products (including intermediates) produced by any aspect of the methods of the invention. The products include libraries, siRNA, shRNA, and any other population produced, which are generally based on the nature of the oligonucleotide(s) used in the methods described herein.

In another aspect, the invention provides reaction mixtures comprising (a) a target miRNA; (b) a FON; (c) a SON; (d) an RNA polymerase; and (c) a DNA polymerase. The reaction mixture could also further comprise enzymes which cleaves RNA from an RNA/DNA hybrid, such as RNase H or cleaves single stranded DNA oligonucleotides.

In another aspect, the invention provides kits for conducting the methods described herein. These kits, in suitable packaging and generally (but not necessarily) containing suitable instructions for performing any of the methods of the invention described herein, including sequencing, detection of sequence; determining presence or absence of a sequence of interest; gene expression profiling; preparation of libraries; preparation of an immobilized nucleic acid (which can be a nucleic acid immobilized on a microarray), and characterizing (including detecting and/or quantifying and/or determining presence or absence of) amplified nucleic acid products generated by the methods of the invention. The kits further comprise one or more components used in the methods of the invention. For example, the invention provides kits that comprise a FON that comprises a sequence which is hybridizable to a miRNA or a potential miRNA sequence and instructions for using the FON in amplifying miRNA. The invention also provides kits that further comprise a SON, and optionally instructions for using the SON in amplifying miRNA. The kits can contain further components, such as any of the enzymes described herein, such as an enzyme which cleaves RNA from an RNA/DNA hybrid (for example, RNase H), DNA polymerase (RNA-dependent or DNA-dependent) and RNA polymerase.

In another aspect, the invention provides systems for affecting the amplification methods described herein. For example, the invention provides systems for amplifying a target small ribonucleic acid, comprising: (a) a FON; (b) a SON; (c) an RNA-dependent DNA polymerase; (d) a DNA-dependent DNA polymerase; (e) an enzyme which cleaves RNA from an RNA/DNA hybrid (such as RNase H); (f) a restrictive enzyme; (g) ncRNA, (h) siRNA, (i) shRNA, and (j) a small molecule immobilized on a solid support. As described herein, systems of the invention generally comprise one or more apparatuses appropriate for carrying out methods of the invention.

EXAMPLE 1

Amplification of mir-9

Figure 9:
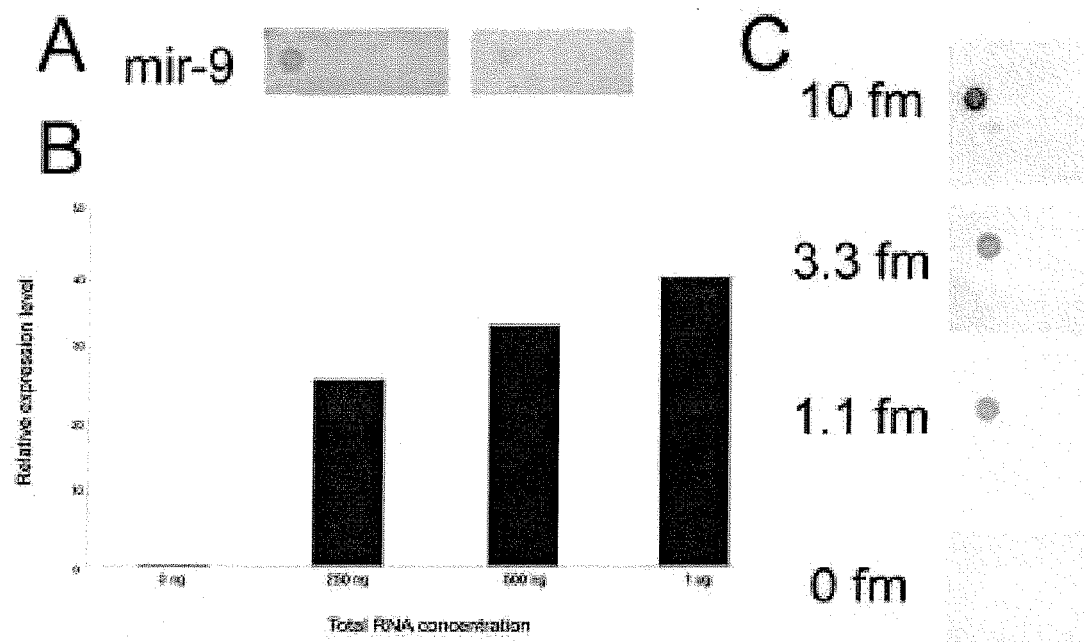
FIG. 9 is a schematic illustrating the ability to identify mir-9 using the SSAM procedure according to the present invention.

The SSAM methodology is demonstrated using mir-9, a miRNA species present in brain. Referring to FIG. 9, total RNA isolated from mouse hippocampus and synthesized mir-9 was used as starting material for mir-9 amplification. The process of amplification consists of five steps: 1) synthesis of the complementary strand of the FON using the target miRNA as primer; 2) digestion of the double stranded FON with the restriction endonuclease BSMI; 3) clearance of single stranded FON with SAv conjugated magnetic beads; 4) RNase digestion of miRNA and attachment of a SON to the FON; 5) amplification of the "signature sequence" of the target miRNA.

Step 1. Synthesis of the complementary strand of the FON. The sequence of the FON;

```
                                       (SEQ. ID NO. 1)
Bio/AAC GAG GAA TGC GGC CAG TGA ATT GTA ATA CGA

CTC ACT ATA GGA TCA TAC AGC TAG ATA A
```

1 fm of FON and 100 ng of total RNA were mixed with following reagents: 4 ul of 5× reverse transcription buffer; 2 ul dNTPs (10 mM); 1 ul DTT (10 mM).

The reaction mixture was incubated in a thermal cycler at 72° C. for 2 minutes and then the temperature was decreased to 55° C. At this point 1 ul of RNase inhibitor (SUPERaseIn, Ambion, Foster City, Calif.; 20 U) and 1 ul of Superscript III (Invitrogen, Carlsbad, Calif.; 200 U) were added into reaction mixture. The total volume was adjusted to 20 ul with 18.2 mega Ohm RNase-free water (Nanopure Diamond, Dubuque, Iowa) and the reaction mixture was further incubated at 55° C. for 30 minutes followed by 65° C. for 15 minutes to stop the reaction by inactivating the enzyme.

Step 2. Digest the double stranded FON with a restriction endonuclease, BsmI.

The DNA synthesis reaction was mixed with 10 ul 10× NEBuffer 2 (New England BioLabs, Ipswich, Mass.), 1 ul BSMI (New England BioLabs; 10 U), and 18.2 mega Ohm RNase-free water to adjust total volume to 100 ul.

The reaction mixture was incubated at 65° C. for 60 minutes followed by 80° C. for 20 minutes to stop the reaction by inactivate the enzyme.

Step 3. Clear single stranded FON with streptavidin conjugated magnetic beads;

Wash 5 ul (50 ug) SAv conjugated magnetic beads twice with water and add in the reaction mix. Incubate the reaction mix with magnetic beads together at 22° C. for 30 minutes. Shake often to mix beads and reaction mix well. Separate beads from reaction mix using a magnetic column.

Step 4. Attach the SON to the FON;

The sequence of SON of mir-9;

```
                                       (SEQ. ID NO. 2)
GGC GCG CCG AAT TCT TCA TAC TCA TAC GTT ATC TAG

CTT CTT TGG TTA TCT AGC TTC TTT GGT TAT CTA GCT
```

Heat SON at 84° C. for 2 minutes and cool down on ice.

Add 1 fm SON, 1 ul RNase H (10 U) into the reaction mix and incubate at 37° C. for 30 minutes. 1 ul 3'-5' exonuclease negative Klenow fragment (5 U) was added at this point and the reaction mix was incubated for another 30 minutes. The reaction was stopped by incubating the reaction mix at 75° C. for 20 minutes to inactivate the enzymes.

Step 5. Amplify the "signature sequence" of the target miRNA using IVT.

The reaction mix was cleaned and concentrated using Vivaspin 500 column (Sartorius, Edgewood, N.Y.). To clean the sample, transfer the whole sample into a Vivaspin 500 column (30,000 MWCO PES), add 500 ul $H_2O$ the column. Spin the column at 15,000 g for 6 minutes. Collect samples into microfuge tubes and adjust the volume of samples to 15 ul. For in vitro transcription, to each 7.5 ul sample, add 4 ul of 5×IVT buffer, 1 ul (2.5 mM) 3 NTPs (A, C, G), 1 ul UTP (100 uM), 0.5 ul RNasin (10 U), 4 ul (80 uCi) $^{33}$P (GE Healthcare, Piscataway, N.J.), and 1 ul T7 RNA polymerase (Epicentre, Madison, Wis.; 1000 U), and the reaction mix was incubated at 37° C. for 4 hours. Radiolabeled probes were hybridized to custom-designed oligonucleotide arrays without further purification.

EXAMPLE 2

Generation of a mir-9 Array

SON of mir-9 is amplified via PCR.

Forward primer: AGC TAG ATA ACC AAA GAA (SEQ. ID NO. 3)

Reverse primer: GGC CAG TGA ATT GTA ATA CGA (SEQ. ID NO. 4)

The PCR reaction mixture comprises 1 fm of SON, 0.1 nm of each forward and reverse primer, 50 μl of 2× AmpliTaq Gold PCR Master Mix (Applied Biosystems, Foster City, Calif.), in a final volume of 100 μl. The amplification conditions are: 95° C. 3 minutes, followed by 50° C. 45 seconds, 68° C. at 1 minute for 40 cycles. The concentration of the PCR product was visualized via agarose gel electrophoresis, and 0.1 ug of PCR product was spotted on nylon membranes.

Membranes were cut to the appropriate size and soaked in 2×SSC buffer prior to arraying. The PCR product was diluted in 2×SSC buffer and denatured at 95° C. for 5 minutes. The denatured PCR product was spotted on the membrane using a slot blot apparatus (Schleicher & Schuell). Spotted arrays were baked at 80° C. in a vacuum oven for 2 h to adhere the nucleic acids to the membrane for downstream applications.

EXAMPLE 3

Detection of the Amplification Products

The detection of the amplification products was performed by hybridization of the amplified sample to oligonucleotides immobilized on a solid support, nylon membranes.

Arrays were prehybridized (2 hours) and hybridized (14-16 hours) in a solution consisting of 6×SSPE, 5× Denhardt's solution, 50% formamide, 0.1% sodium dodecyl sulfate (SDS), and denatured salmon sperm DNA (200 μg/ml) at 42° C. in a rotisserie oven. Following hybridization, arrays were washed sequentially in 2×SSC/0.1% SDS, 1×SSC/0.1% SDS and 0.5×SSC/0.1% SDS for 15 min each at 37° C. Arrays were placed in a phosphor screen for 24 hours and developed on a phosphor imager (GE Healthcare). Hybridization signal intensity was determined by utilizing ImageQuant TL array analysis program (GE Healthcare).

EXAMPLE 4

Screening for New miRNAs

This application comprises the following five basic steps; 1) synthesis of complementary strand of the FON using the target ncRNA/miRNA/small polynucleotide sequence as a primer; 2) digest the double stranded FON with a restriction endonuclease, BsmI; 3) clear single stranded FON with SAv conjugated magnetic beads; 4) attach the SON to the FON; 5) cloning and sequencing the resultant clones.

Step 1. Synthesis of complementary strand of the FON using a potential miRNA as primer. Sequence of FON:

(SEQ. ID NO. 5)
Bio/AAC GAG GAA TGC GGC CAG TGA ATT GTA ATA CGA

CTC ACT ATA GGA NNN NNN NNN NN

Where N represents A, C, G, or T 1 fm of FON and 500 ng of total RNA were mixed with following reagents: 4 ul of 5× reverse transcription buffer; 2 ul dNTPs (10 mM); 1 ul DTT (10 mM).

The reaction mixture was incubated in a thermal cycler at 72° C. for 2 minutes and then the temperature was decreased to 55° C. At this point 1 ul of RNasin (Ambion; 20 U) and 1 ul of Superscript III (Invitrogen; 200 U) were added into reaction mixture. The total volume was adjusted to 20 ul with 18.2 mega Ohm RNase-free water and the reaction mixture was further incubated at 55° C. for 30 minutes followed by 65° C. for 15 minutes to stop the reaction by inactivating the enzyme.

Step 2. Digest the double stranded FON with a restriction endonuclease, BsmI.

The DNA synthesis reaction was mixed with 10 ul 10× NEBuffer 2 (New England BioLabs, Ipswich, Mass.), 1 ul BSMI (New England BioLabs; 10 U), and 18.2 mega Ohm RNase-free water to adjust total volume to 100 ul.

The reaction mixture was incubated at 65° C. for 60 minutes followed by 80° C. for 20 minutes to stop the reaction by inactivate the enzyme.

Step 3. Clear single stranded FON with SAv conjugated magnetic beads.

Wash 5 ul (50 ug) streptavidin conjugated magnetic beads twice with water and add in the reaction mix. Leave the reaction mix with magnetic beads together at 22° C. for 30 minutes. Shake often to mix beads and reaction mix well. Separate beads from reaction mix using a magnetic column.

Step 4. Attach the SON to the FON.

The sequence of SON:

GGC GCG CCG AAT TCN NNN NNN NNN NN (SEQ. ID NO. 6)

Where N represents A, C, G, or T.

Heat 1 fm SON at 84° C. for 2 minutes and cool down on ice.

Add 1 fm SON, 1 ul RNase H (10 U) into the reaction mix and incubate at 37° C. for 30 minutes. 1 ul 3'-5' exonuclease negative Klenow fragment (5 U) was added at this point and the reaction mix was incubated further 30 minutes. The reaction was stopped by incubating the reaction mix at 75° C. for 20 minutes to inactivate the enzymes.

Step 5. Cloning and sequencing the final clones.

Cut a cloning vector, Bluescript with a restriction enzyme, EcoR V, to yield a blunt end. Mix the reaction products from Step 4 with cloning vector in 1× ligation buffer and 1 ul (40 U). the ligation mixture was incubated at 16° C. overnight. 2 ul of ligation product was used to transform 50 ul of E.coli competent cells and the transformed bacteria were selected by ampicillin. The transformed colonies were screened at first with direct colony PCR with vector primers and promising clones were confirmed.

What is claimed is:

1. A method of generating a signature sequence of a target ncRNA, comprising the steps of:
   hybridizing the target ncRNA to a first oligonucleotide to form a hybridized molecule;
   extending the hybridized molecule to form a double-stranded RNA/DNA hybrid molecule;
   cleaving the double-stranded RNA/DNA hybrid molecule with a ribonuclease to form a cleaved molecule with an overhang at the 3' end that is at least partially complementary to the target ncRNA;
   hybridizing a second oligonucleotide to the overhang at the 3' end of the cleaved molecule to form a complex; and
   generating a signature sequence from the complex.

2. The method of claim 1, wherein the step of hybridizing the target ncRNA to the first oligonucleotide comprises incubating a sample containing the target ncRNA with the first oligonucleotide.

3. The method of claim 2, wherein the first oligonucleotide is single stranded with a binding molecule conjugated at 5' end.

4. The method of claim 2, wherein the first oligonucleotide is partially double stranded and the sense strand has a 3' overhang complementary to the ncRNA and the antisense strand has a binding molecule conjugated at 3' end.

5. The method of claim 1, wherein the step of extending the hybridized ncRNA sequence and first oligonucleotides to generate double stranded RNA/DNA hybrid molecule is performed in the presence of a DNA polymerase.

6. The method of claim 1, wherein the step of hybridizing a second oligonucleotide to the cleaved RNA/DNA hybrid molecule comprises incubating a sample containing the RNA/DNA hybrid molecule with a second oligonucleotide.

7. The method of claim 6, wherein step of hybridizing the target ncRNA to a first oligonucleotide comprises incubating the sample containing the target ncRNAs with a pool of first oligonucleotides.

8. The method of claim 1, wherein the step of generating a signature sequence is performed in the presence of DNA polymerase.

9. The method of claim 1, further comprising the step of removing any free first oligonucleotides before incubating the cleaved double stranded RNA/DNA hybrid molecule with the second oligonucleotide.

10. The method of claim 9, wherein the step of removing any free first oligonucleotides comprises enzymatically digesting any single stranded first oligonucleotides with an exonuclease.

11. The method of claim 9, wherein the step of removing any free first oligonucleotides comprises a pair of binding molecules present in the free first oligonucleotides and an insoluble support.

12. The method of claim 9, wherein the step of removing any free first oligonucleotides comprises a combination of digesting the double stranded RNA/DNA hybrid molecule and clearing any free first oligonucleotide with a pair of binding molecules present in the free first oligonucleotides and an insoluble support.

13. A method of amplifying at least one target ncRNA sequence, comprising the steps of:
   hybridizing the at least one target ncRNA to a first oligonucleotide to form a hybridized molecule;
   extending the hybridized molecule to form a double-stranded RNA/DNA hybrid molecule;
   cleaving the double-stranded RNA/DNA hybrid molecule to form a cleaved molecule with an overhang at the 3' end that is at least partially complementary to the target ncRNA;
   hybridizing a second oligonucleotide to the overhang at the 3' end of the cleaved molecule to form a complex;
   generating a signature sequence from the complex; and
   amplifying the signature sequence.

14. The method of claim 13, wherein the signature sequence is amplified using at least one amplification process selected from the group consisting of one directional polymerase chain reaction, limited cycle polymerase chain reaction, in vitro transcription, and combinations thereof.

15. The method of claim 13, further comprising the step of removing any free second oligonucleotides before amplifying the signature sequence.

16. The method of claim 13, wherein the second oligonucleotide is single stranded with a binding molecule conjugated at 5' end.

17. The method of claim 13, wherein the second oligonucleotide is partially double stranded with a sense strand having a 3' overhang complementary to the ncRNA and an antisense strand having a binding molecule conjugated at 3' end.

18. The method of claim 16, further comprising the step of removing any free second oligonucleotides before amplifying the signature sequence.

19. The method of claim 18, wherein step of removing any free second oligonucleotides comprises enzymatically digesting any single stranded second oligonucleotides with an exonuclease.

* * * * *